(12) United States Patent
Matsutani

(10) Patent No.: US 6,350,125 B1
(45) Date of Patent: Feb. 26, 2002

(54) CONTRA-ANGLE DENTAL HANDPIECE

(75) Inventor: Kanji Matsutani, Takanezawa-machi (JP)

(73) Assignee: Mani, Inc., Tochigi (JP)

( * ) Notice: Subject to any disclaimer, the term of this patent is extended or adjusted under 35 U.S.C. 154(b) by 0 days.

(21) Appl. No.: 09/645,665

(22) Filed: Aug. 24, 2000

(30) Foreign Application Priority Data

Aug. 27, 1999 (JP) .............................. 11-240677

(51) Int. Cl.[7] ................................ A61C 1/07
(52) U.S. Cl. ........................................ 433/118
(58) Field of Search ................. 433/118, 122

(56) References Cited

U.S. PATENT DOCUMENTS

| | | |
|---|---|---|
| 3,969,823 A | 7/1976 | Nakamishi |
| 4,175,324 A * | 11/1979 | Arai ........................ 433/122 |
| 4,205,444 A | 6/1980 | Weissman |
| 4,498,868 A | 2/1985 | Schuss |
| 5,120,220 A | 6/1992 | Butler |
| 5,145,369 A * | 9/1992 | Lustig et al. ................ 433/122 |
| 5,599,143 A | 2/1997 | Dusing |
| 5,980,248 A | 11/1999 | Kusakabe et al. |

* cited by examiner

Primary Examiner—Cary E. O'Connor
(74) Attorney, Agent, or Firm—Muramatsu & Associates

(57) ABSTRACT

A contra-angle dental handpiece is capable of rotating a cutting tool in the forward direction when the cutting tool is in the most advanced position in a root canal of a tooth and preventing the reverse rotation of the cutting tool when the cutting tool is retracted therefrom. The contra-angle dental handpiece includes a rotation shaft for rotating a dental cutting tool about a rotation axis, a drive shaft for rotating the rotation shaft, and a drive mechanism for driving the dental cutting tool in a backward and forward direction of the rotation axis and for intermittently rotating the dental cutting tool only in the forward rotational direction about the rotation axis when the cutting tool is at around a most advanced position in a root canal of a tooth.

17 Claims, 7 Drawing Sheets

CONTRA-ANGLE DENTAL HANDPIECE

FIELD OF THE INVENTION

This invention relates to a handpiece for dental use, and more particularly, to a contra-angle dental handpiece to be used by a dental practitioner for cutting or drilling a root canal of a tooth.

BACKGROUND OF THE INVENTION

In forming a root canal of a tooth, dental cutting tools such as a dental reamer or a dental file is generally used. The dental reamer and/or dental file may be operated manually or with use of a handpiece with a drive mechanism. A dental reamer has a relatively gentle (large lead) spiral cutting edge which is rotated in a root canal for cutting a surrounding inner wall of the root canal. In contrast, a dental file has a spiral cutting edge having a lead smaller than that of the dental reamer for cutting the surrounding inner wall of the root canal. These are the basic ways in using the reamer and file, however, the reamer and file are also used by incorporating the back and forth movements as well as rotational movements at the same time.

Thus, a dental handpiece for operating such a dental reamer or file is sometimes capable of driving the reamer or file both the back and forth movements and rotational movements. This invention is directed to a contra-angle dental handpiece in which the handpiece has a shape which is bent about a right angle.

As is known in the art, a root canal is narrower toward a distal end and is also curved as a whole. Thus, it is practically impossible to visually monitor when cutting and forming the root canal until the distal end thereof, thus, involving cut-and-try like work. Further, when applying the rotational movement to the reamer or file, a continuous application of only one direction of rotation or repeated applications of both forward and reverse directions of rotation in the curved root canal tend to cause metal fatigue to the dental cutting tool (reamer or file) because of the continuous or alternate load. Furthermore, in this situation, torsional load applied to the dental cutting tool will be increased, which may break the cutting tool. To avoid the damage to the cutting tool, it is known in the art that there is a type of dental handpiece which is designed to drive the dental cutting tool both in a "rotary mode" to provide a rotational movement and a "reciprocating model" to provide a back and forth movement to the cutting tool.

FIG. 6 shows an example of conventional contra-angle dental handpiece proposed in Japanese Patent Laid-Open Publication No. 4-300534. FIG. 6 is a cross sectional view showing essential components of the dental handpiece. As noted above, the dental handpiece in this example is able to apply both the rotational movement (rotary mode) and the back and forth movement (reciprocating mode) to the cutting tool (reamer or file).

The dental handpiece includes a frame 3, a tool chucker 2 and a cap holder 4. The tool chucker 2 for freely mounting a cutting tool 1 (such as reamer and file) therein is attached to the frame 3 in a manner rotational about an rotational axis a. The cap holder 4 is rotatable but is not removable from the frame 3. The upper end of the cutting tool 1 has a hook which is latched by a projection of the cap holder 4 when the cap holder 4 is rotated in a small degree. Consequently, the cutting tool 1 is installed in the dental handpiece through the cap holder 4 and is moved in the direction of the rotational axis a in the reciprocating mode and is rotated about the rotational axis a in the rotary mode in response to the movement of the tool chucker 2.

The handpiece of FIG. 6 further includes an inner sleeve 5 and an outer sleeve 6 around the tool chucker 2. The outer sleeve 6 is fitted to the tool chucker 2 through, for example, a pressed-in or screwed-in process and moves both in the rotary mode and reciprocating mode with the movements of the tool chucker 2. The inner sleeve 5 is positioned between the tool chucker 2 and the outer sleeve 6 and independently rotates and moves back and forth.

The frame 3 of the handpiece is bent at about right angle where a crank shaft 7 is rotatably provided in a direction perpendicular to the cutting tool 1 (rotation axis a). The crank shaft 7 is driven by a drive mechanism such as a motor (not shown). The crank shaft 7 has, at its end, an eccentric shaft 8 and an eccentric ball 9 at the end of the eccentric shaft 8.

The outer sleeve 6 has a guide groove 6a in which the eccentric shaft 8 of the crank shaft 7 is engaged. When the crank shaft 7 rotates, the eccentric shaft 8 rotates accordingly, thereby driving the outer sleeve 6 in the direction of the rotation axis a, although there is no rotation of the outer sleeve 6. With the back and forth (reciprocating) movement of the outer sleeve 6, the tool chucker 2 moves back and forth accordingly.

The surrounding wall of the inner sleeve 5 has a long hole 5a in the direction of the rotation axis a which is engaged with the ball 9 formed on the end of the crank shaft 7. Thus, when the crank shaft 7 rotates, the ball 9 rotates accordingly, thereby rotating the inner sleeve 5 in the forward and reverse direction about the rotation axis a (rotary mode). However, the inner wall 5 is not driven by the ball 9 back and forth in the direction of the rotation axis a (reciprocating mode).

In the foregoing configuration of the handpiece of FIG. 6, by the rotation of the crank shaft 7, the eccentric shaft 8 rotates accordingly, thereby driving the tool chucker 2 in the reciprocating mode and the rotary mode. Namely, in the reciprocating mode, the handpiece drives the tool chucker in the direction of the rotation axis a. In the rotary mode, the handpiece rotates the tool chucker 2 about the rotation axis a. In other words, the cutting tool 1 (reamer or file) moves back and forth in the direction of the rotation axis a while rotates about the rotation axis a in the forward and reverse direction at the same time.

The foregoing example of the conventional handpiece further includes a switch means so as to switch between the operation involving only the reciprocating mode (back and forth movement in the direction of axis a) driven by the eccentric shaft 8 and the other operation involving both the reciprocating mode and the rotary mode (forward and reverse rotation about the axis a) driven by the eccentric shaft 8 and the ball 9. Such switching mechanism is unrelated to the point of the present invention, and thus, no further description is given here.

As in the foregoing, with use of the handpiece of FIG. 6, a root canal of a tooth can be effectively formed by the reciprocating mode and the rotary mode of the cutting tool 1. As noted above, the reciprocating mode involves the back and forth movement of the cutting tool 1 in the axial direction of the axis a and the rotary mode involves the forward and reverse rotation of the cutting tool 1, which is typically less than one rotation, i.e., 360°.

In the process of forming a root canal of a tooth, it is important to carefully operate the handpiece so that the cutting tool such as a reamer or file is driven in the reciprocating movement as well as the rotary movement. As shown in FIG. 7, in the cutting process of a curved root canal 10, the cutting tool 1 is sent to a root opening 10a at the end of the root canal 10 and is rotated to cut the tissue in the area shown by the dotted line, thereby forming a seat at the root opening 10a. Under this situation, if the cutting tool 1 is driven by the continuous rotation in one direction at a high speed, or high speed repetition of the forward and reverse rotation, metal fatigue may be caused, which may damage the cutting tool 1.

Further, in forming the root canal of the tooth, the debris generated by cutting the inner wall of the root canal must be effectively carried away to the outside. This is because the debris is full of germs causing inflammation and suppuration after the dental treatment if the debris is not sufficiently removed.

In the root canal treatment based on the manual operation of the cutting tool, it is desirable to repeat the process of rotating the cutting tool in the forward direction at the position most advanced and retreating the cutting tool therefrom. It is very important to rotate the cutting tool in the forward direction by less than one rotation, such as by a ¼ or ⅕ rotation at the intended cutting position (most advanced position) in the root canal.

This is because, first, such a repetition of the process can minimize the stress brought to the cutting tool, thereby avoiding the damage and extending the life time of the cutting tool. An example of rotation angle is sufficiently less than an angle in which the cutting tool has a problem in digging into the root canal wall, such as less than 180°, preferably in the range about 20°–45°.

Second, the debris of the root canal produced by the rotation of the cutting tool having a spiral cutting edge has to be removed toward the outside by the forward rotation of the spiral cutting edge.

Third, as shown in FIG. 7, since the root canal is curved, the cutting tool 1 is curved along the root canal. Under this situation, the end of the cutting tool 1 contacts the outer curve of the root canal 10. Thus, if the cutting tool 1 is rotated when retracted (backward movement in the reciprocating mode), an intermediate portion of the root canal may be cut, forming a step 10b as shown in FIG. 8 or cutting the root canal excessively.

Therefore, a contra-angle handpiece is desired to have a capability that it can rotate the cutting tool in the forward direction at the intended cutting location, i.e., most advanced position, in the root canal.

As noted above, the conventional contra-angle handpiece of FIG. 6 can drive the cutting tool in the back and forth in the direction of axis a as well as forward and reverse rotation about the axis a. However, the handpiece of FIG. 6 is not specifically designed to apply the forward rotation to the cutting tool when advancing the cutting tool in the root canal or where at the most advanced position (drilling position) in the root canal.

In the example of handpiece of FIG. 6, it is possible to achieve the forward rotation of the cutting tool while advancing forward in the root canal if positions of the eccentric shaft 8 and the ball 9 are so adjusted. However, in such a case, the cutting tool rotates in the reverse direction as well when retracted back in the root canal. This may cause excessive fatigue on the cutting tool or sending back the debris to the inside of the root canal. Moreover, since it is not designed with specific intention to rotate the cutting tool at the most advanced position in the root canal, an excessive cut, such as the step of FIG. 8, may be caused in the root canal.

SUMMARY OF THE INVENTION

This invention has been made to solve the problems involved in the dental handpiece in the conventional technology.

It is, therefore, an object of the present invention to provide a contra-angle dental handpiece which is capable of rotating the cutting tool in the forward direction when the cutting tool is in the most advanced position (cutting position).

It is another object of the present invention to provide a contra-angle dental handpiece which is capable of preventing the reverse rotation of the cutting tool when the cutting tool is retracted from the most advanced position in the root canal, thereby promoting the removal of debris generated by cutting the tissue of the root canal.

In the present invention, a contra-angle dental handpiece includes a rotation shaft for rotating a dental cutting tool about a rotation axis, a drive shaft for rotating the rotation shaft, and a drive mechanism for driving the dental cutting tool in a backward and forward direction of the rotation axis and for at least rotating the dental cutting tool in the forward direction about the rotation axis when the cutting tool is at around a most advanced position in a root canal of a tooth. The contra-angle dental handpiece further includes a tool chucker for attaching the cutting tool to the dental handpiece.

The drive mechanism in the contra-angle dental handpiece is comprised of a receptacle means provided directly or indirectly on the cutting tool to produce the rotation of the cutting tool, and a coupling means provided on the drive shaft to temporarily couple with the receptacle means during the rotation of the drive shaft to move the receptacle means in the backward and forward direction in the direction of said rotation axis. The coupling means rotates the receptacle means in the forward rotational direction when the receptacle means is moving in the forward direction of the rotation axis and releases the coupling to the receptacle means when the receptacle means is moving in the backward direction of the rotation axis.

More particularly, the drive mechanism in the contra angle dental handpiece is comprised of first and second circular plates provided on the tool chucker in a parallel fashion with a predetermined distance therebetween, and an engagement projection connected to an end of the drive shaft and is projected in a space between the first and second circular plates. The second circular plate has a plurality of grooves one of which receives said engagement projection therein when the engagement projection rotates by the rotation of the drive shaft. The engagement projection drives the first circular plate to move the tool chucker backward in the direction of the rotation axis and drives the second circular plate to move the tool chucker forward in the direction of the rotation axis. The engagement projection rotates the tool chucker only in the forward rotational direction when the tool chucker is moving in the forward direction of the rotation axis.

The drive shaft may be comprised of first and second drive shafts each being operated independently from each other wherein the first drive shaft drives the forward and backward movement of the tool chucker and the second drive shaft drives the rotation of the tool chucker.

The contra-angle dental handpiece may further comprises a first spring means for pressing the first circular plate in the forward direction of the rotation axis and a second spring for pressing the second circular plate in the backward direction of the rotation axis.

In a further embodiment, the receptacle means is a first bevel gear connected directly or indirectly to the cutting tool and the coupling means is a second bevel gear connected to the drive shaft. The first bevel gear is larger than the second bevel gear in diameter.

According to the present invention, the contra-angle handpiece can drive the dental cutting tool such as a dental reamer or a dental file both in the reciprocating mode and the rotary mode, and can apply at least the forward rotation to the cutting tool when the cutting tool is in the most advanced position in the root canal. In the present invention, it is possible to effectively prevent the cutting tool from being damaged and extend the life time of the cutting tool. The dental handpiece of the present invention can promote removal of the debris from the root canal and can establish a clean root canal without involving excessive cutting in the inner wall of the root canal.

DETAILED DESCRIPTION OF THE PREFERRED EMBODIMENTS

The contra-angle dental handpiece of the present invention will be described in detail with reference to the accompanying drawings wherein like numerals refer to like parts throughout. The cross sectional view of FIG. 1 is a first embodiment of the contra-angle handpiece of the present invention and shows an example of structure of essential components in the dental handpiece.

Figure 6:
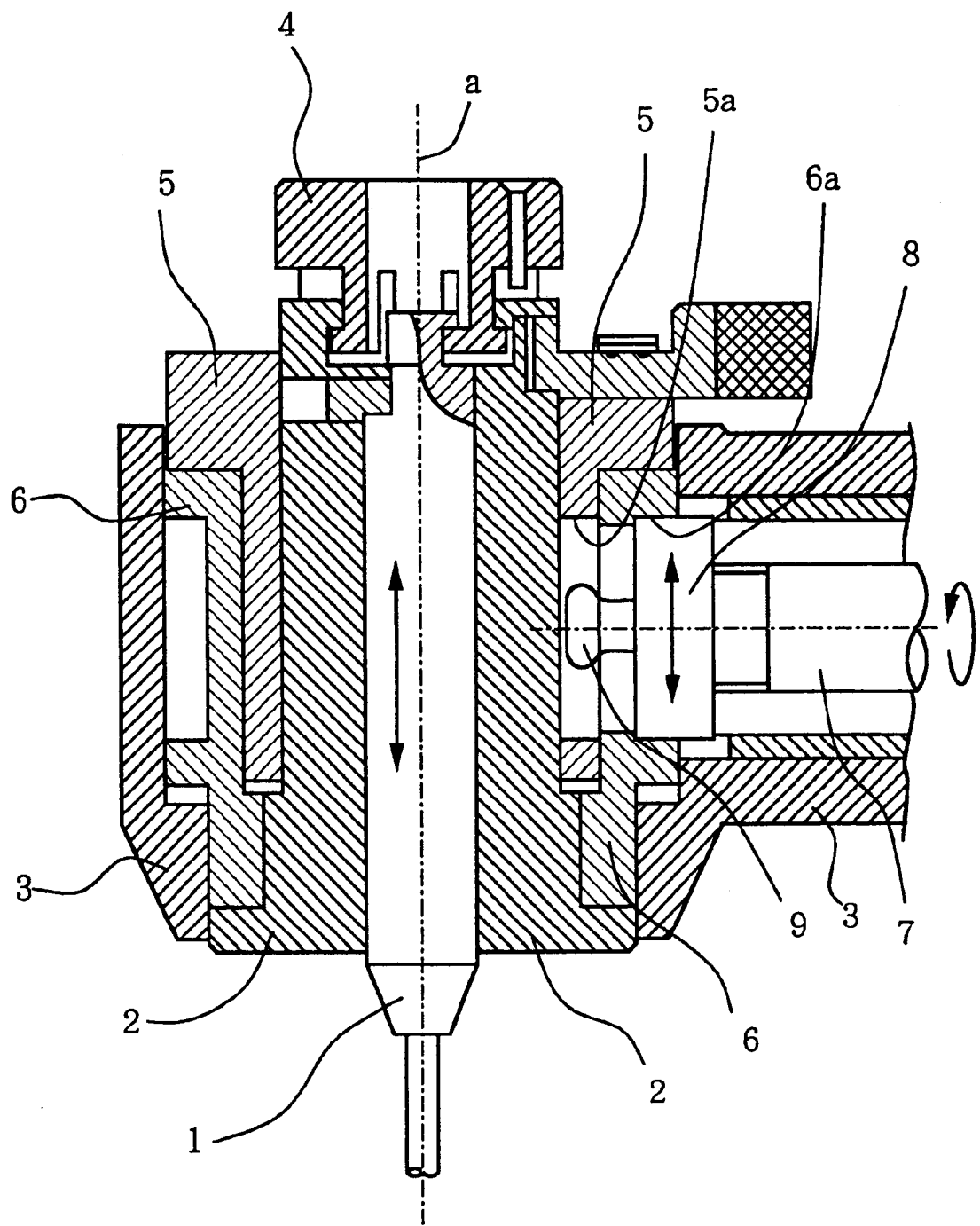
FIG. 6 is a cross sectional view showing an example of basic structure of the contra-angle dental handpiece in the conventional technology.
Figure 7:
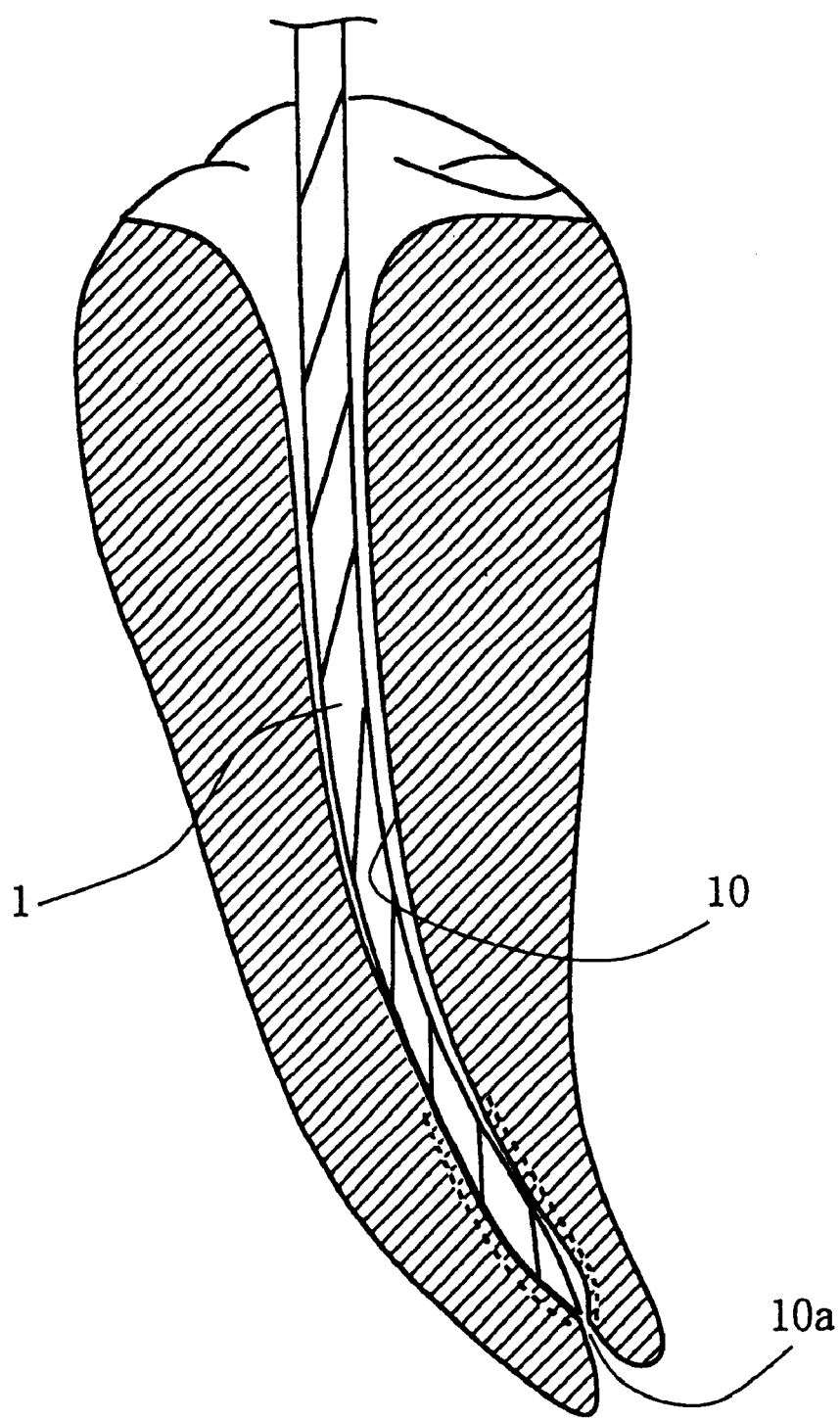
FIG. 7 is a schematic diagram showing a cross sectional view for forming a root canal of a tooth by a cutting tool.
Figure 8:
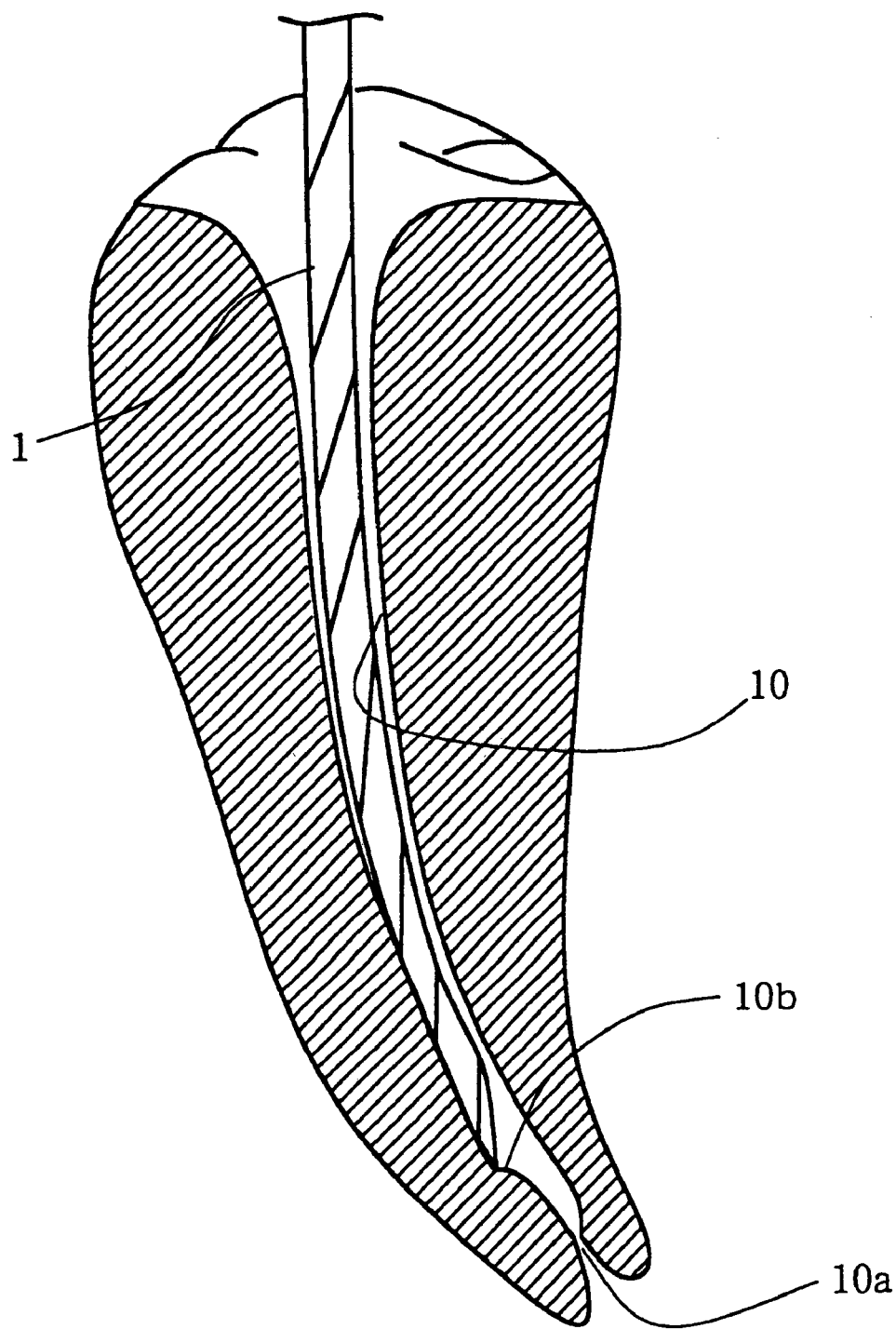
FIG. 8 is a schematic diagram showing a cross sectional view for showing a problem of forming a step in the root canal in the conventional technology.

A cutting tool 1, such as a dental reamer or a dental file, is attached to the dental handpiece through a tool chucker (rotation shaft) 2. The tool chucker 2 is identical to the one described with respect to the conventional example of FIG. 6 and is supported on a frame 3 of the dental handpiece. The tool chucker 2 is so configured that it can rotate about the rotational axis a (rotary mode) as well as advance and retract in the direction of the rotational axis a (reciprocating mode). Since the cutting tool 1 is fixedly mounted on the tool chucker 2, it can move both in the rotary mode and the reciprocating mode in response to the movement of the tool chucker 2.

Figure 1:
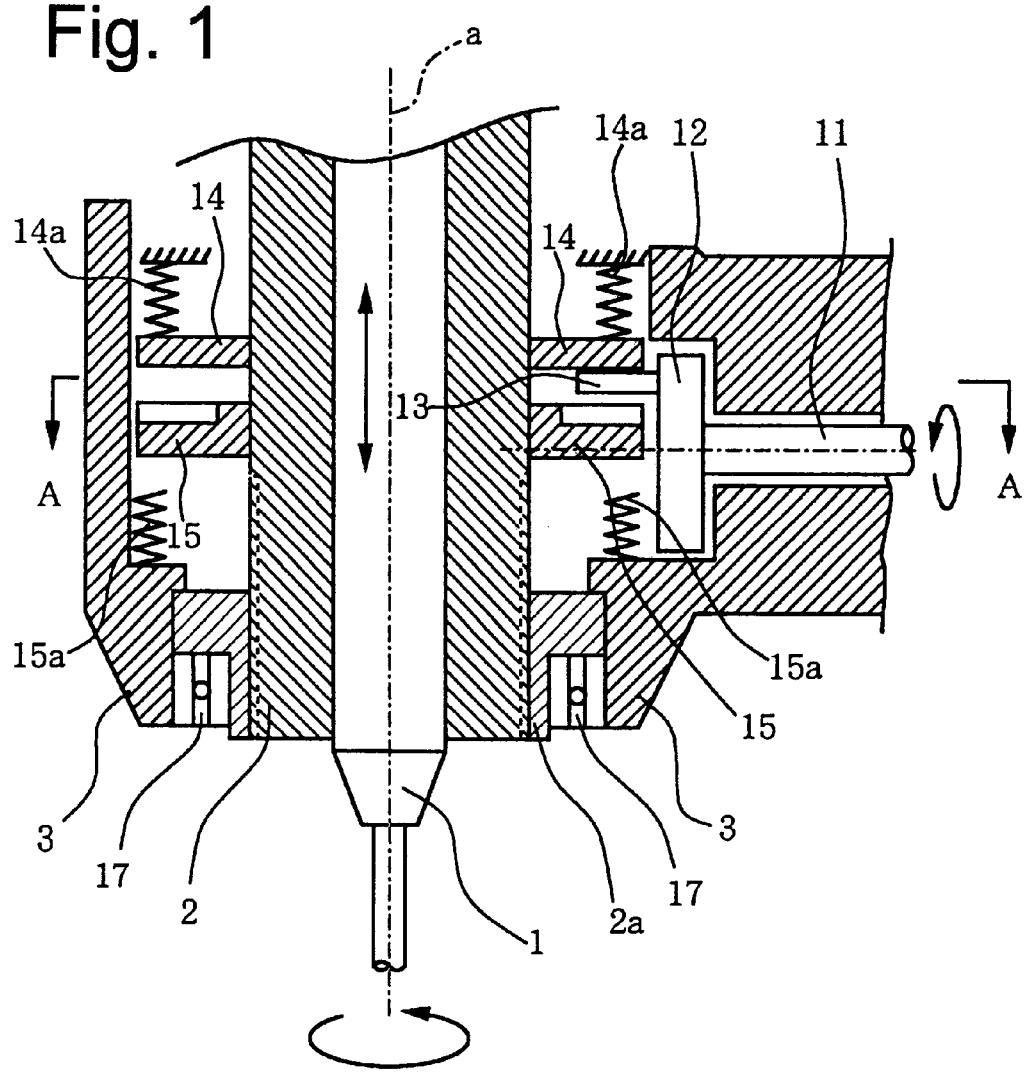
FIG. 1 illustrates a cross sectional view of one embodiment of a contra-angle dental handpiece embodying features of the present invention.

The frame 3 extends in the right hand direction of FIG. 1 in perpendicular to the rotational axis a (rotation shaft) wherein a drive shaft 11 is rotationally supported at its center. The drive shaft 11 has, at its end, a large diameter portion 12 on which an engagement projection 13 is formed at its end. An example of the engagement projection 13 is a stick or rod having a circular shape in cross section. The engagement projection 13 is attached, in an eccentric manner, to the large diameter portion 12.

Figure 2A:
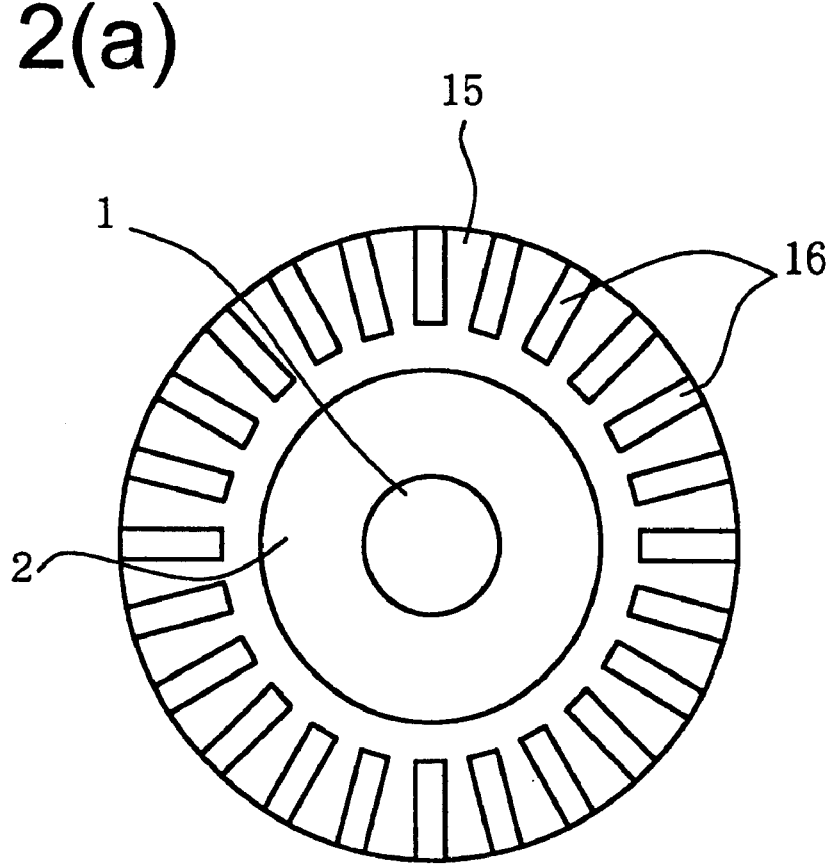
FIG. 2(a) is a top view of the circular plate 15 as seen in the direction of the arrows A—A in FIG. 1.

Two circular plates 14 and 15 are provided at around an intermediate position of the tool chucker 2 with a predetermined distance between which the engagement projection 13 is loosely projected. The circular plate (upper plate) 14 has a flat lower surface while the circular plate (lower plate) 15 has a large number of engagement grooves 16 radially formed on the circumference of its upper surface as shown in FIG. 2(a). Further, spring means 14a and 15a are provided to press the circular plates 14 and 15, respectively. The spring means 14a is to press the circular plate 14 downwardly and the spring means 15a is to press the circular plate 15 upwardly. In FIG. 2, the spring means 14a contacts the circular plate 14 while the spring means 15a is slightly apart from the circular plate 15.

The dental handpiece of FIG. 1 further includes a coupling member 2a having a spline coupling groove (not shown) between an lower end of the tool chucker 2 and the frame 3. Further, a one-way (directional) clutch 17 is provided between the coupling member 2a and the frame 3. The one-way clutch 17 is so configured to allow the forward rotation of the tool chucker 2 and to disallow the reverse rotation of the tool chucker 2. Alternatively, other means such as a ratchet can be used to achieve the same effect of the one-way clutch 17. Although the coupling member 2a rotates about the rotational axis a along with the tool chucker 2, the coupling member 2a will not move in the reciprocating mode because of the spline structure thereof. The above noted means for prohibiting the reverse rotation may be unnecessary depending on the other conditions.

When the drive shaft 11 rotates in a predetermined direction in response to a power source such as a motor (not shown), the engagement projection 13 rotates about the drive shaft 11. Thus, the tip end of the engagement projection 13 moves along a circle 18 in FIG. 2(b) illustrated by a single dotted line.

Figure 4:
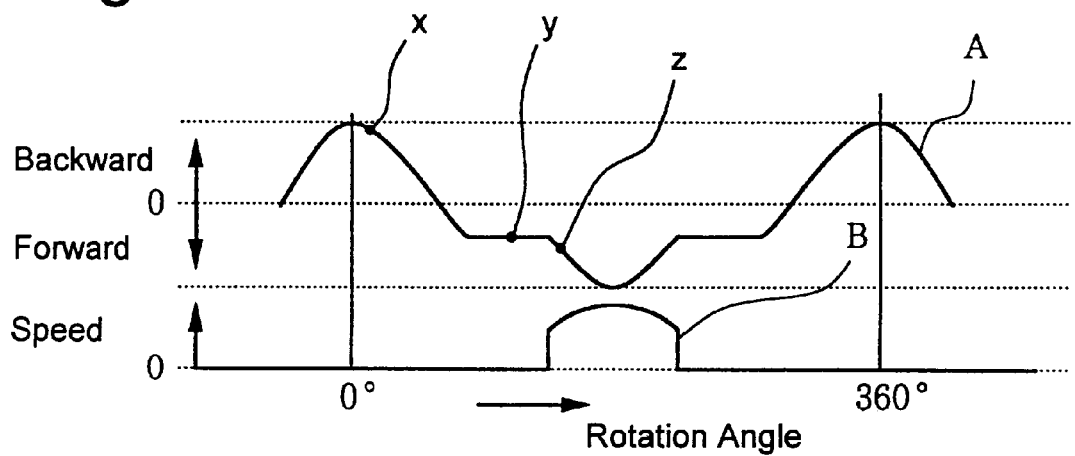
FIG. 4 is a timing chart showing timing relationships between the reciprocating movement and the rotary movement of the two circular plates in response to the rotation of the drive shaft.
Figure 2B:
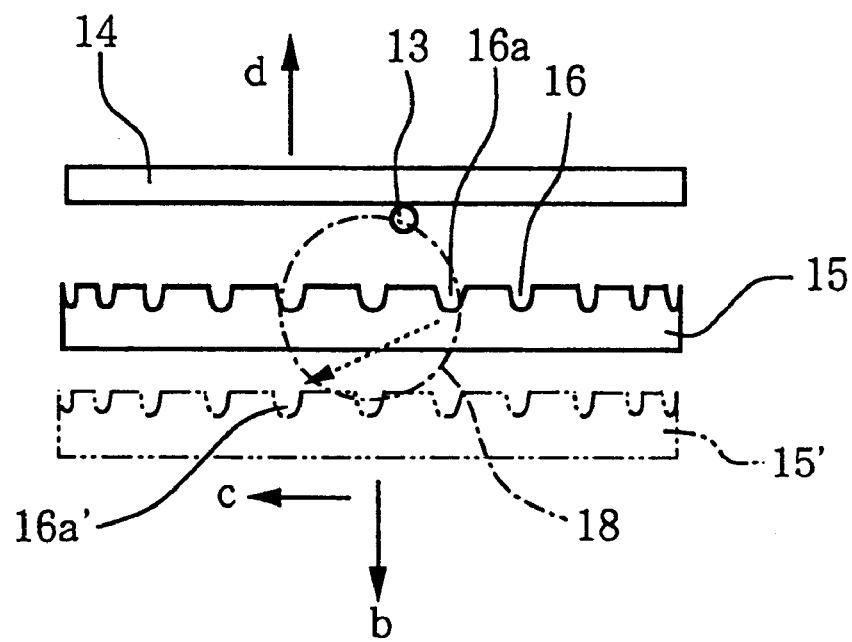
FIG. 2(b) is a schematic diagram showing an operation involving an engagement projection on a drive shaft and engagement grooves provided on a circular plate.

Assuming the rotation of the engagement projection 13 on the circle 18 of FIG. 2(b) is in the clockwise direction, the circular plates 14 and 15 operate in a manner shown in FIGS. 3 and 4. In FIG. 4, the line A indicates the backward and forward movements (reciprocating mode) of the circular plates 14 and 15 while the line B indicates the rotation speed of the circular plates 14 and 15. The vertical axis of FIG. 4 is a vertical position (backward forward position) for the line A, and the rotation speed for the line B. The horizontal axis of FIG. 4 is the rotation angle of the drive shaft or the engagement projection.

Figure 3A:
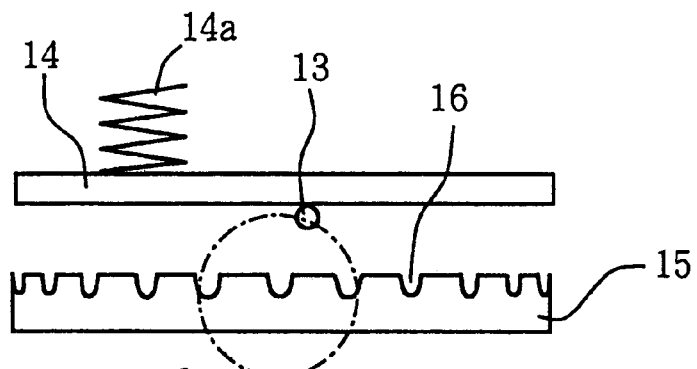
FIGS. 3(a)–3(c) show the relationships between the reciprocating and rotary movements involved in the two circular plates and the rotary movement of the engagement projection on the drive shaft in the dental handpiece of the present invention.
Figure 3B:
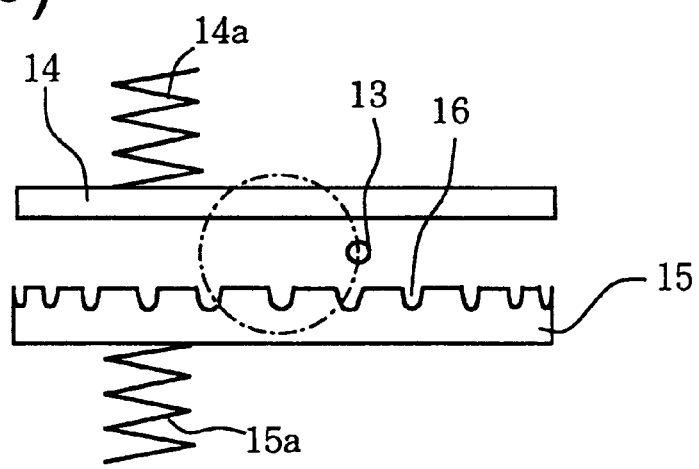

FIG. 3(a) shows a situation corresponding to the curve x on the line A of FIG. 4 where the engagement projection 13 starts from the circular plate 14 and rotates in the clockwise direction. Since the circular plate 14 is pressed downwardly by the spring means 14a, by the rotation of the engagement projection 13, the circular plate 14 moves downward along with the engagement projection 13. When the engagement projection 13 further rotates (moves downward), the circular plates 14 and 15 stop at the position where the two spring means 14a and 15a balance with each other as shown in FIG. 3(b). This situation is indicated by the curve y on the line A of FIG. 4. In this situation, the engagement projection 13 does not contact either the plates 14 or 15.

Figure 3C:
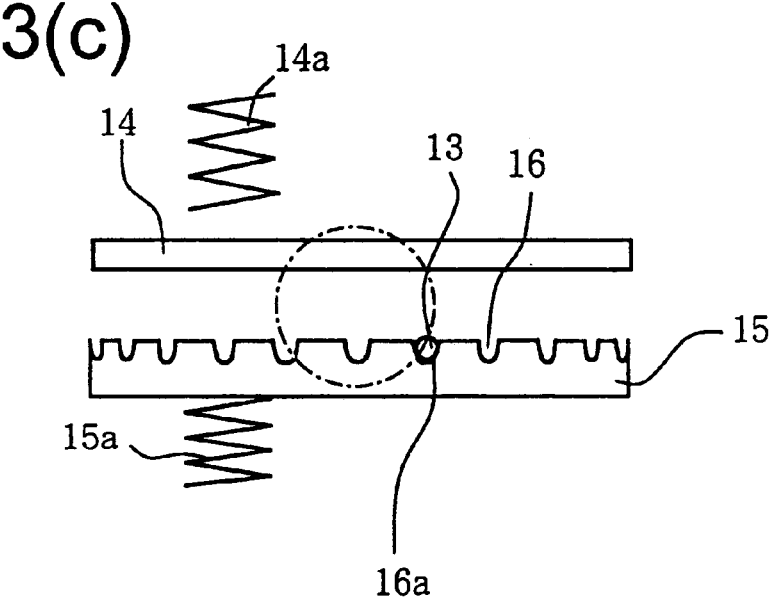

When the engagement projection 13 further rotates, as shown in FIG. 3(c), it engages with one of the engagement grooves 16 on the circular plate 15. This position is shown by the curve z on the line A of FIG. 4. While engaging with the engagement groove 16, the engagement projection 13 further rotates along the circle 18, thereby pressing down the circular plate 15 until the position of the circular plate 15 shown by the two dotted line of FIG. 2(b).

Therefore, the tool chucker 2 advances (moves downward) in the direction shown by the arrow b of FIG. 2(b) while rotates at the same time in the direction shown by the arrow c of FIG. 2(b) by an angle corresponding to the positions between 16a and 16a' of the engagement grooves on the circular plate 15. This situation is also shown in FIG. 4 wherein the circular plate 15 in the curve z which increases the rotation speed and then decreases the rotation speed after its peak as illustrated by the line B.

The engagement projection 13 presses down the circular plate 15 when rotating about ½–¼ rotation on the circumference of the circle 18 and rotates the circular plate 15 in the direction of the arrow c. After that, the engagement projection 13 disengages from the engagement groove 16. Thus, in the last ½–¼ rotation, the engagement projection 13 presses the circular plate 14 upwardly in the direction d of FIG. 2(b).

As noted above, the engagement projection 13 driven by the drive shaft 11 contacts the circular plate 14 and presses the circular plate 14 upwardly. Thus, the cutting tool 1 moves backward in the reciprocating mode. Since the circular plate 14 is not provided with radial engagement grooves such as the grooves 16 on the circular plate 15, there is no rotation of the circular plate 14, i.e., no reverse rotation of the cutting tool 1.

Accordingly, the cutting tool 1 rotates in the forward direction at around the most advance position in the root canal of a tooth, but will not rotate when the cutting tool 1 moves backward after this position. The directional clutch associated with the tool chucker 2 and the frame 3 further ensure no reverse rotation of the cutting tool 1 when going backward in the root canal.

Since the amount of backward and forward movements (the arrows d and b in FIG. 2(b)) of the circular plates 14 and 15 are identical to one another, the cutting tool 1 repeats the same movements by the rotation of the drive shaft 11. The spring means 14a and 15a promote and limit the movements of the circular plates 14 and 15. However, the spring means 14a and 15a are not essential to the basic operation of the dental handpiece of the present invention and can be omitted depending on the other conditions.

Figure 5:
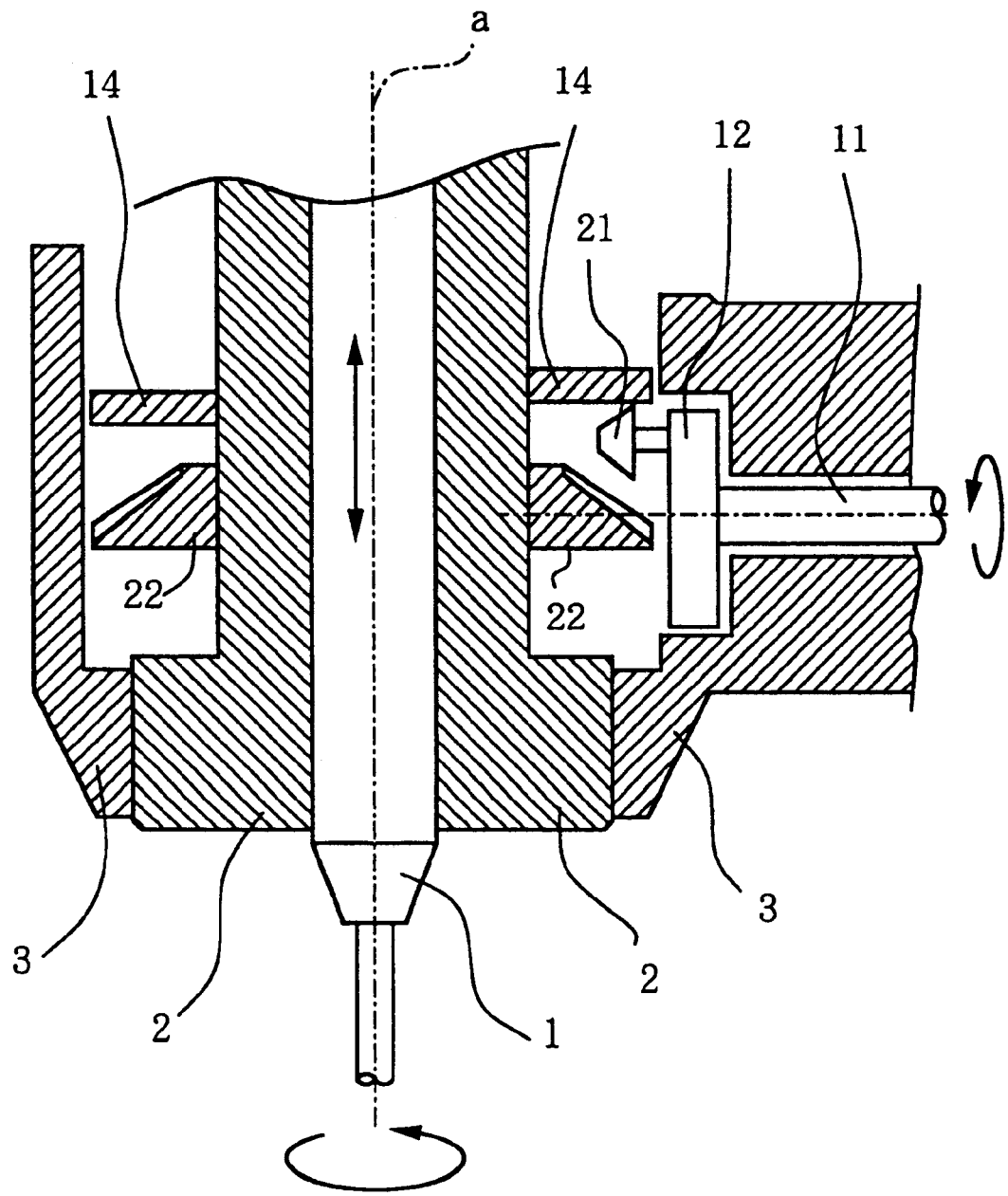
FIG. 5 illustrates a cross sectional view of another embodiment of the contra-angle dental handpiece embodying features of the present invention.

FIG. 5 shows an example of structure in the second embodiment of the present invention. In this example, bevel gears are employed corresponding to the engagement projections and radial engagement grooves in the first embodiment. The second embodiment is described mainly with respect to the differences from the first embodiment. A bevel gear 21 is mounted on the large diameter portion 12 on the drive shaft 11. The bevel gear 21 is eccentric on the large diameter portion 12 relative to the axis of the drive shaft 11. Another bevel gear 22 is provided on the tool chucker 2 in stead of the circular plate 15 of the first embodiment. Preferably, as shown in FIG. 5, the bevel gear 21 is smaller than the bevel gear 22 in diameter.

By the rotation of the drive shaft 11, the bevel gear 21 rotates about the drive shaft 11, and eventually engages with the bevel gear 22. By the further rotation of the drive shaft, the bevel gear 21 drives down the bevel gear 22, thus, advances the cutting tool 1, and, at the same time, rotates the cutting tool 1 about the rotation shaft (rotational axis a) in the forward rotational direction.

It is also possible to provide a spring at the bottom of the bevel gear 22 to press the bevel gear 22 in the upward direction. In this arrangement, the bevel gears 21 and 22 constantly engage with each other, and thus, the rotational movement and the reciprocating movement of the cutting tool 1 are produced always at the same time.

In a further modification, the dental handpiece may include two drive shafts, each being driven by an independent power source such as a motor. In such an arrangement, one of the drive shafts is used for producing the backward and forward movement (reciprocating mode) while the other is used for driving the small bevel gear for producing the rotational movement (rotary mode) of the cutting tool. Thus, the cutting tool can be forwardly rotated at the most advanced position in the root canal while, at other positions, it can be selectively controlled whether the forward rotation or no rotation should be conducted.

In this embodiment of using the bevel gears, spring means similar to the spring means 14a and 15a in the first embodiment may be employed. Depending on the setting of the spring means, it can be arranged so that the small bevel gear 21 and the large bevel gear 22 to engage with each other all the time. In this arrangement, for example, the small bevel gear 21 may be driven by an independent power source so that the large bevel gear is rotated slowly and constantly in response to the rotation of the small bevel gear.

As has been described above, the contra-angle handpiece of the present invention can drive the dental cutting tool such as a dental reamer or a dental file both in the reciprocating mode and the rotary mode, and can apply at least the forward rotation to the cutting tool when the cutting tool is in the most advanced position in the root canal. In the present invention, it is possible to effectively prevent the cutting tool from being damaged and extend the life time of the cutting tool. The dental handpiece of the present invention can promote removal of the debris from the root canal and form a clean root canal without involving excessive cutting in the inner wall of the root canal.

Although only a preferred embodiment is specifically illustrated and described herein, it will be appreciated that many modifications and variations of the present invention are possible in light of the above teachings and within the purview of the appended claims without departing the spirit and intended scope of the invention.

What is claimed is:

1. A contra-angle dental handpiece comprising:
    a rotation shaft for rotating a dental cutting tool about a rotation axis;
    a drive shaft for rotating the rotation shaft; and
    a drive mechanism for driving the dental cutting tool in a backward and forward direction of the rotation axis and for intermittently rotating the dental cutting tool only in a forward rotational direction about the rotation axis while preventing rotation of the dental cutting tool in a backward rotational direction when the cutting tool is at around a most advanced position.

2. A contra-angle dental handpiece as defined in claim 1, wherein said rotation shaft is a tool chucker for attaching the cutting tool to the dental handpiece.

3. A contra-angle dental handpiece as defined in claim 2, wherein said drive mechanism is comprised of:
    a receptacle means provided directly or indirectly on the tool chucker to produce the rotation of said tool chucker; and a coupling means provided on said drive shaft to temporarily couple with said receptacle means during the rotation of said drive shaft to move said receptacle means in the backward and forward in the direction of said rotation axis;

wherein said coupling means rotates said receptacle means only in the forward rotational direction when said receptacle means is moving in the forward direction of the rotation axis and releases the coupling to the receptacle means when said receptacle means is moving in the backward direction of the rotation shaft.

4. A contra-angle dental handpiece as defined in claim 2, wherein said drive mechanism is comprised of first and second circular plates provided on said tool chucker in a parallel fashion with a predetermined distance therebetween, and an engagement projection connected to an end of said drive shaft and is projected in a space between the first and second circular plates;

wherein said second circular plate has a plurality of grooves one of which receives said engagement projection therein when said engagement projection rotates by the rotation of said drive shaft:

and wherein said engagement projection drives said first circular plate to move said tool chucker backward in the direction of said rotation axis and drives said second circular plate to move said tool chucker forward in the direction of said rotation axis, wherein said engagement projection rotates said tool chucker only in the forward rotational direction when said tool chucker is moving in the forward direction of the rotation axis.

5. A contra-angle dental handpiece as defined in claim 4, wherein said engagement projection is eccentrically formed on the end of said drive shaft so that it rotates about said drive shaft with a predetermined diameter between said first and second circular plates.

6. A contra-angle dental handpiece as defined in claim 4, wherein said drive shaft is comprised of first and second drive shafts each independently operating from each other wherein said first drive shaft drives said forward and backward movement of said tool chucker and said second drive shaft drives said rotation of said tool chucker.

7. A contra-angle dental handpiece as defined in claim 4, further comprising a first spring means for pressing said first circular plate in the forward direction in said direction of said rotation axis and a second spring for pressing said second circular plate in the backward direction in said direction of said rotation axis.

8. A contra-angle dental handpiece as defined in claim 7, wherein said second circular plate is a first bevel gear connected to said tool chucker and said engagement projection is a second bevel gear eccentrically connected to said end of said drive shaft, and wherein said first bevel gear is larger than said second bevel gear in diameter.

9. A contra-angle dental handpiece as defined in claim 1, wherein said drive mechanism is comprised of:

a receptacle means provided directly or indirectly on the cutting tool to produce the rotation of said cutting tool; and a coupling means provided on said drive shaft to temporarily couple with said receptacle means during the rotation of said drive shaft to move said receptacle means in the backward and forward in the direction of said rotation axis;

wherein said coupling means rotates said receptacle means in the forward rotational direction when said receptacle means is moving in the forward direction of the rotation axis and releases the coupling to the receptacle means when said receptacle means is moving in the backward direction of the rotation axis.

10. A contra-angle dental handpiece as defined in claim 9, wherein said receptacle means is a first bevel gear connected directly or indirectly to said cutting tool and said coupling means is a second bevel gear connected to said drive shaft, and wherein said first bevel gear is larger than said second bevel gear in diameter.

11. A contra-angle dental handpiece as defined in claim 1, wherein said dental cutting tool is so controlled that there is no rotation in the reverse direction when said dental cutting tool is moved in the backward direction of said rotation axis.

12. A contra-angle dental handpiece as defined in claim 1, wherein said drive mechanism includes a member for preventing the reverse rotation of said dental cutting tool.

13. A contra-angle dental handpiece as defined in claim 12, wherein said member for preventing the reverse rotation of said dental cutting tool is a one-way clutch.

14. A contra-angle dental handpiece as defined in claim 1, wherein said drive mechanism drives said dental cutting tool in the backward and forward direction of the rotation axis and rotates said dental cutting tool only in the forward rotational direction about said rotation axis when said dental cutting tool is at around the most advanced position in a root canal of a tooth.

15. A contra-angle dental handpiece as defined in claim 1, wherein said drive mechanism rotates said dental cutting tool about said rotation axis only in the forward rotational direction when said dental cutting tool is at around the most advanced position and prohibits any rotation of said dental cutting tool at any other positions.

16. A contra-angle dental handpiece as defined in claim 1, wherein an angle of said dental cutting tool in said forward rotational direction is less than 180°.

17. A contra-angle dental handpiece as defined in claim 1, wherein an angle of said dental cutting tool in said forward rotational direction is within 25°–45°.

* * * * *